United States Patent
Polonka et al.

(10) Patent No.: US 8,105,617 B2
(45) Date of Patent: *Jan. 31, 2012

(54) CATIONIC COPOLYMERS FORMULATED WITH PIGMENTED COSMETIC COMPOSITIONS EXHIBITING RADIANCE WITH SOFT FOCUS

(75) Inventors: Jack Polonka, Peekskill, NY (US); John Brian Bartolone, Bridgeport, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 433 days.

This patent is subject to a terminal disclaimer.

(21) Appl. No.: 12/335,553

(22) Filed: Dec. 16, 2008

(65) Prior Publication Data

US 2009/0208442 A1   Aug. 20, 2009

Related U.S. Application Data

(60) Provisional application No. 61/029,654, filed on Feb. 19, 2008.

(51) Int. Cl.
  *A61Q 19/00* (2006.01)
  *A61K 8/00* (2006.01)
  *A61K 47/00* (2006.01)
  *A61K 8/02* (2006.01)

(52) U.S. Cl. ......... 424/401; 424/78.08; 424/59; 424/63; 424/69; 514/772

(58) Field of Classification Search .................. None
  See application file for complete search history.

(56) References Cited

U.S. PATENT DOCUMENTS

| | | | |
|---|---|---|---|
| 5,700,452 A * | 12/1997 | Deckner et al. | 424/59 |
| 6,344,185 B1 * | 2/2002 | Argus et al. | 424/59 |
| 7,015,279 B2 * | 3/2006 | Braun et al. | 524/815 |
| 7,514,496 B2 * | 4/2009 | Amalric et al. | 524/501 |
| 7,780,954 B2 * | 8/2010 | Polonka et al. | 424/59 |
| 7,794,740 B2 * | 9/2010 | Cohen et al. | 424/401 |
| 2004/0091444 A1 | 5/2004 | Loffler et al. | |
| 2005/0014893 A1 | 1/2005 | Braun et al. | |
| 2007/0259803 A1 | 11/2007 | Carnali et al. | |
| 2008/0131385 A1 | 6/2008 | Roso et al. | |

FOREIGN PATENT DOCUMENTS

| | | |
|---|---|---|
| EP | 1 277 458 A1 | 7/2002 |
| WO | 97/13497 | 4/1997 |
| WO | 02/41856 A1 | 5/2002 |
| WO | 2005/070382 A1 | 8/2005 |

OTHER PUBLICATIONS

PCT International Search Report PCT/EP2009/051027, Jun. 18, 2009.
Co-Pending Application—Polonka et al.; Filed: May 29, 2008; Entitled: Glow And Sunless Tanning Color Enhancement By Cationic Copolymers.
Co-Pending Application—Polonka et al.; Filed: Dec. 16, 2008; Entitled: Cationic Copolymer And Starches Formulated Cosmetic Compositions Exhibiting Radiance With Soft Focus.

* cited by examiner

*Primary Examiner* — Lakshmi Channavajjala
(74) *Attorney, Agent, or Firm* — Milton L. Honig

(57) ABSTRACT

A cosmetic composition is provided which includes a silicone elastomer, a cationic copolymer with monomeric units selected from at least an acryloylethyl tri($C_1$-$C_3$ alkyl)ammonium salt, and light reflecting platelet shaped particles. The compositions are particularly useful to impart radiance as well as soft focus effects onto the skin. A particular useful cationic copolymer is that of acrylamide/acryloylethyl trimethylammonium chloride/tris(hydroxymethyl)acrylamidomethane copolymer.

5 Claims, No Drawings

CATIONIC COPOLYMERS FORMULATED WITH PIGMENTED COSMETIC COMPOSITIONS EXHIBITING RADIANCE WITH SOFT FOCUS

BACKGROUND OF THE INVENTION

1. Field of the Invention

The invention relates to compositions for improving the appearance of skin, particularly to provide good coverage over imperfections such as pores and uneven skin tone, while retaining a natural skin appearance.

2. The Related Art

A matte effect is desired for users of color cosmetics. The matte finish overcomes the shiny effect engendered by greasy skin, particularly under hot and humid conditions. Absorbent fillers such as talc, silica, kaolin and other inorganic particulates have been used to achieve the effect by their optical properties.

Imperfect skin can be hidden in two ways through manipulation of light transmission. In the first, components of the color cosmetic may simply reflect light back toward the source. An alternative approach is referred to as achieving a soft focus effect. Here the incoming light is distorted by scattering (lensing). Components of the color cosmetic in this mechanism operate as lenses to bend and twist light into a variety of directions.

While it is desirable to hide imperfect skin through a matte effect, there is also a desire to achieve a healthy skin radiance. A cosmetic covering that is too opaque hides the skin under a paint-like coating. Imperfections are hidden but there is no radiance. Where light transmission is insufficiently hindered, the opposite occurs. Here the glow may be healthy but aesthetically displeasing skin topography and color may now be apparent.

U.S. Pat. No. 5,997,890 (Sine et al.), U.S. Pat. No. 5,972,359 (Sine et al.), and U.S. Pat. No. 6,174,533 B1 (SaNogueira, Jr.) are all directed to topical compositions to provide good coverage of skin imperfections. The solution proposed by these documents is the use of a metal oxide with a refractive index of at least about 2 and a neat primary particle size of from about 100 to about 300 nm. Preferred particulates are titanium dioxide, zirconium oxide and zinc oxide.

Silicone gelling agents such as crosslinked organopolysiloxane elastomers because of their excellent skinfeel properties have been found useful in make-up compositions. For instance, U.S. Pat. No. 5,266,321 (Shukuzaki et al.) discloses an oily make-up composition comprised of a silicone gel crosslinked elastomer, titanium dioxide, mica and iron oxides. Japanese patent application 61-194009 (Harashima) describes a make-up composition comprising a cured organopolysiloxane elastomer powder and pigments which may be selected from talc, titanium dioxide, zinc oxide and iron oxides.

A challenge which has not been fully met by the known art is delivery of a composition with appropriate optics to achieve both soft focus and radiance properties in a system that still provides excellent skinfeel.

SUMMARY OF THE INVENTION

A cosmetic composition is provided which includes:
(i) from about 0.01 to about 30% by weight of a crosslinked silicone elastomer;
(ii) from about 0.1 to about 20% by weight of a cationic copolymer having monomer units of acryloylethyl tri($C_1$-$C_3$ alkyl)ammonium salt;
(iii) from about 0.1 to about 5% by weight of light reflecting platelet shaped particles; and
(iv) a cosmetically acceptable carrier.

DETAILED DESCRIPTION OF THE INVENTION

Now it has been found that a soft focus effect with radiance can be obtained by a combination of a crosslinked silicone elastomer, a cationic copolymer with at least one of the monomer unit being an acryloylethyl tri($C_1$-$C_3$ alkyl)ammonium salt, and light reflecting platelet shaped particles.

Crosslinked Silicone Elastomer

A component of the present invention is a crosslinked silicone (organopolysiloxane) elastomer. No specific restriction exists as to the type of curable organopolysiloxane composition that can serve as starting material for the crosslinked silicone elastomer. Examples in this respect are addition reaction-curing organopolysiloxane compositions which cure under platinum metal catalysis by the addition reaction between SiH-containing diorganopolysiloxane and organopolysiloxane having silicon-bonded vinyl groups; condensation-curing organopolysiloxane compositions which cure in the presence of an organotin compound by a dehydrogenation reaction between hydroxyl terminated diorganopolysiloxane and SiH-containing diorganopolysiloxane; condensation-curing organopolysiloxane compositions which cure in the presence of an organotin compound or a titanate ester, by a condensation reaction between an hydroxyl terminated diorganopolysiloxane and a hydrolyzable organosilane (this condensation reaction is exemplified by dehydration, alcohol-liberating, oxime-liberating, amine-liberating, amide-liberating, carboxyl-liberating, and ketone-liberating reactions); peroxide-curing organopolysiloxane compositions which thermally cure in the presence of an organoperoxide catalyst; and organopolysiloxane compositions which are cured by high-energy radiation, such as by gamma-rays, ultraviolet radiation, or electron beams.

Addition reaction-curing organopolysiloxane compositions are preferred for their rapid curing rates and excellent uniformity of curing. A particularly preferred addition reaction-curing organopolysiloxane composition is prepared from:
(A) an organopolysiloxane having at least 2 lower alkenyl groups in each molecule;
(B) an organopolysiloxane having at least 2 silicon-bonded hydrogen atoms in each molecule; and
(C) a platinum-type catalyst.

The crosslinked siloxane elastomer of the present invention may either be an emulsifying or non-emulsifying crosslinked organopolysiloxane elastomer or combinations thereof. The term "non-emulsifying," as used herein, defines crosslinked organopolysiloxane elastomer from which polyoxyalkylene units are absent. The term "emulsifying," as used herein, means crosslinked organopolysiloxane elastomer having at least one polyoxyalkylene (e.g., polyoxyethylene or polyoxypropylene) unit.

Particularly useful emulsifying elastomers are polyoxyalkylene-modified elastomers formed from divinyl compounds, particularly siloxane polymers with at least two free vinyl groups, reacting with Si—H linkages on a polysiloxane backbone. Preferably, the elastomers are dimethyl polysiloxanes crosslinked by Si—H sites on a molecularly spherical MQ resin.

Preferred silicone elastomers are organopolysiloxane compositions available under the INCI names of dimethicone/ vinyl dimethicone crosspolymer, dimethicone crosspolymer and Polysilicone-11. Ordinarily these materials are provided as a 1-30% crosslinked silicone elastomer dissolved or suspended in a dimethicone fluid (usually cyclomethicone). For purposes of definition "crosslinked silicone elastomer" refers to the elastomer alone rather than the total commercial compositions which also include a solvent (eg dimethicone) carrier.

Dimethicone/vinyl dimethicone crosspolymers and dimethicone crosspolymers are available from a variety of suppliers including Dow Corning (9040, 9041, 9045, 9506 and 9509), General Electric (SFE 839), Shin Etsu (KSG-15, 16, 18 [dimethicone/phenyl vinyl dimethicone crosspolymer]), and Grant Industries (Gransil™ line of materials), and lauryl dimethicone/vinyl dimethicone crosspolymers supplied by Shin Etsu (e.g, KSG-31, KSG-32, KSG-41, KSG-42, KSG-43, and KSG-44).

Other suitable commercially available silicone elastomer powders include vinyl dimethicone/methicone silsesquioxane crosspolymers from Shin-Etsu sold as KSP-100, KSP-101, KSP-102, KSP-103, KSP-104, KSP-105, and hybrid silicone powders that contain a fluoroalkyl group or a phenyl group sold by Shin-Etsu as respectively KSP-200 and KSP-300.

The crosslinked silicone elastomers of the present invention may range in concentration from about 0.01 to about 30%, preferably from about 0.1 to about 10%, optimally from about 0.5 to about 2% by weight of the cosmetic composition. These weight values exclude any solvent such as cyclomethicone found in commercial "elastomer" silicones such as the Dow Corning products DC 9040 and DC 9045. For instance, the amount of crosslinked silicone elastomer in DC 9040 and DC 9045 is between 12 and 13% by weight.

Most preferred as the silicone elastomer is DC 9045 which has a D5 cyclomethicone swelled elastomer particle size (based on volume and calculated as spherical particles) which averages about 38 micron, and may range from about 25 to about 55 micron.

Cationic Copolymer

Cationic copolymers of the present invention incorporate as one of the repeating units an acryloylethyl tri($C_1$-$C_3$ alkyl) ammonium salt. The term "salt" for this monomer unit may be but is not limited to chloride, bromide, sulfate, sulphonate, nitrate, tosylate, phosphate and phosphonate. The term "copolymer" means at least two different monomer repeating units, preferably three or more different monomer repeating units. Monomer units that crosslink are particularly useful.

Monomers forming the copolymer with the acryloylethyl tri($C_1$-$C_3$ alkyl)ammonium salt monomer units include: styrene, acrylic acid, methacrylic acid, vinyl chloride, vinyl acetate, vinyl pyrrolidone, isoprene, vinyl alcohol, vinyl methylether, chloro-styrene, dialkylamino-styrene, maleic acid, acrylamide, methacrylamide, tris(hydroxymethyl)-acrylamidomethane and mixtures thereof. Where the term "acid" appears, the term means not only the free acid but also $C_1$-$C_{30}$ alkyl esters, anhydrides and salts thereof. Preferably but not exclusively the salts of the acid may be anions such as ammonium, alkanolammonium, alkali metal and alkaline earth metal salts. Most preferred are the ammonium and alkanolammonium salts.

Most preferred for purposes of this invention as the cationic copolymer is acrylamide/acryloylethyl trimethylammonium chloride/tris(hydroxymethyl)-acrylamidomethane copolymer. Commercial availability is under the trademark 7688 MP available from Seppic Inc.

Number average molecular weight of the copolymers according to the invention may range from about 1,000 to about 3,000,000, preferably from about 3,000 to about 100,000, optimally from about 10,000 to about 80,000.

Amounts of the copolymer may range from about 0.1 to about 20%, preferably from about 0.5 to about 10%, more preferably from about 1 to about 7%, and optimally from about 1.5 to about 5% by weight of the composition.

Light Reflecting Platelet Shaped Particles

A further necessary component of compositions according to the present invention is that of light reflecting platelet shaped particles. These particles will have an average particle size $D_{50}$ ranging from about 10,000 to about 30,000 nm. The refractive index of these particles are preferred to be at least about 1.8, generally from about 1.9 to about 4, more preferably from about 2 to about 3, optimally between about 2.5 and 2.8.

Illustrative but not limiting examples of light reflecting particles are bismuth oxychloride (single crystal platelets) and titanium dioxide coated mica. Suitable bismuth oxychloride crystals are available from EM Industries, Inc. under the trademarks Biron® NLY-L-2X CO and Biron® Silver CO (wherein the platelets are dispersed in castor oil); Biron® Liquid Silver (wherein the particles are dispersed in a stearate ester); and Nailsyn® IGO, Nailsyn® II C2X and Nailsyn® II Platinum 25 (wherein the platelets are dispersed in nitrocellulose). Most preferred is a system where bismuth oxychloride is dispersed in a $C_2$-$C_{40}$ alkyl ester such as in Biron® Liquid Silver.

Among the suitable titanium dioxide coated mica platelets are materials available from EM Industries, Inc. These include Timiron® MP-10 (particle size range 10,000-30,000 nm), Timiron® MP-14 (particle size range 5,000-30,000 nm), Timiron® MP-30 (particle size range 2,000-20,000 nm), Timiron® MP-101 (particle size range 5,000-45,000 nm), Timiron® MP-111 (particle size range 5,000-40,000 nm), Timiron® MP-1001 (particle size range 5,000-20,000 nm), Timiron® MP-155 (particle size range 10,000-40,000 nm), Timiron® MP-175 (particle size range 10,000-40,000), Timiron® MP-115 (particle size range 10,000-40,000 nm), and Timiron® MP-127 (particle size range 10,000-40,000 nm). Most preferred is Timiron® MP-111. The weight ratio of titanium dioxide coating to the mica platelet may range from about 1:10 to about 5:1, preferably from about 1:1 to about 1:6, more preferably from about 1:3 to about 1:4 by weight. Advantageously the preferred compositions will generally be substantially free of titanium dioxide outside of that required for coating mica.

Coatings for mica other than titanium dioxide may also be suitable. Silica coatings are such an alternative.

The amount of the light reflecting platelet shaped particles may range from about 0.1 to about 5%, preferably from about 0.5 to about 3%, more preferably from about 0.8 to about 2%, optimally from about 1 to about 1.5% by weight of the composition.

Advantageously compositions of the present invention may include a non-coated mica. These mica particles can also be platelets but of thinner and smaller particle size than the coated micas mentioned above. Particularly preferred is Satin Mica, available from Merck-Rona. These are useful to remove any excessive glitter imparted by the light scattering platelets. Advantageously the particle size of the non-coated mica is no higher than 15,000 nm and an average (volume) particle size ranging from 1,000 to 10,000 nm, preferably from 5,000 to 8,000 nm.

The amount of the non-coated mica may range from about 0.05 to about 2%, preferably from about 0.1 to about 1.5%, optimally from about 0.4 to about 0.8% by weight of the composition.

Cosmetic Carrier and Optional Components

Compositions of this invention will also include a cosmetically acceptable carrier. Amounts of the carrier may range from about 1 to about 99.9%, preferably from about 70 to about 95%, optimally from about 80 to about 90% by weight of the composition. Among the useful carriers are water, emollients, fatty acids, fatty alcohols, thickeners and combinations thereof. The carrier may be aqueous, anhydrous or an emulsion. Preferably the compositions are aqueous, especially water and oil emulsions of the W/O or O/W or triplex W/O/W variety. Water when present may be in amounts ranging from about 5 to about 95%, preferably from about 20 to about 70%, optimally from about 35 to about 60% by weight.

Emollient materials may serve as cosmetically acceptable carriers. These may be in the form of silicone oils, natural or synthetic esters and hydrocarbons. Amounts of the emollients may range anywhere from about 0.1 to about 95%, preferably between about 1 and about 50% by weight of the composition.

Silicone oils may be divided into the volatile and nonvolatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to $0.1 \, m^2/s$ at 25° C. Among the preferred nonvolatile emollients useful in the present compositions are the polydimethyl siloxanes having viscosities from about $1 \times 10^{-5}$ to about $4 \times 10^{-4}$ $m^2/s$ at 25° C.

Among the ester emollients are:

a) Alkyl esters of saturated fatty acids having 10 to 24 carbon atoms. Examples thereof include behenyl neopentanoate, isononyl isonanonoate, isopropyl myristate and octyl stearate.

b) Ether-esters such as fatty acid esters of ethoxylated saturated fatty alcohols.

c) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.

d) Wax esters such as beeswax, spermaceti wax and tribehenin wax.

e) Sugar ester of fatty acids such as sucrose polybehenate and sucrose polycottonseedate.

Natural ester emollients principally are based upon mono-, di- and tri-glycerides. Representative glycerides include sunflower seed oil, cottonseed oil, borage oil, borage seed oil, primrose oil, castor and hydrogenated castor oils, rice bran oil, soybean oil, olive oil, safflower oil, shea butter, jojoba oil and combinations thereof. Animal derived emollients are represented by lanolin oil and lanolin derivatives. Amounts of the natural esters may range from about 0.1 to about 20% by weight of the compositions.

Hydrocarbons which are suitable cosmetically acceptable carriers include petrolatum, mineral oil, $C_{11}$-$C_{13}$ isoparaffins, polybutenes, and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, oleic, linoleic, linolenic, hydroxystearic and behenic acids.

Fatty alcohols having from 10 to 30 carbon atoms are another useful category of cosmetically acceptable carrier. Illustrative of this category are stearyl alcohol, lauryl alcohol, myristyl alcohol, oleyl alcohol and cetyl alcohol.

Thickeners can be utilized as part of the cosmetically acceptable carrier of compositions according to the present invention. Typical thickeners include crosslinked acrylates (e.g. Carbopol 982®), hydrophobically-modified acrylates (e.g. Carbopol 1382®), polyacrylamides (e.g. Sepigel 305®), acryloylmethylpropane sulfonic acid/salt polymers and copolymers (e.g. Aristoflex HMB® and AVC®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Inorganics may also be utilized as thickeners, particularly clays such as bentonites and hectorites, fumed silicas, calcium carbonate and silicates such as magnesium aluminum silicate (Veegum®). Amounts of the thickener may range from 0.0001 to 10%, usually from 0.001 to 1%, optimally from 0.01 to 0.5% by weight of the composition.

Humectants may be employed in the present invention. These are generally polyhydric alcohol-type materials. Typical polyhydric alcohols include glycerol, propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of adjunct humectant may range anywhere from 0.5 to 50%, preferably between 1 and 15% by weight of the composition.

Compositions of the present invention may be in any form. These forms may include lotions, creams, roll-on formulations, sticks, mousses, aerosol and non-aerosol sprays and fabric (e.g. nonwoven textile)-applied formulations. Particularly useful are nonwoven cloths of polypropylene or cotton/polyester impregnated with dihydroxyacetone and a cationic copolymer of the present invention.

Surfactants may also be present in compositions of the present invention. Total concentration of the surfactant when present may range from about 0.1 to about 30%, preferably from about 0.1 to about 15%, optimally from about 0.5 to about 2% by weight of the composition. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) and trialkylamine oxides are also suitable nonionic surfactants.

Preferred anionic surfactants include soap, alkyl ether sulfates and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, $C_8$-$C_{20}$ sarcosinates, $C_8$-$C_{20}$ acyl lactylates, sulfoacetates and combinations thereof.

Useful amphoteric surfactants include cocoamidopropyl betaine, $C_{12}$-$C_{20}$ trialkyl betaines, sodium lauroamphoacetate, and sodium laurodiamphoacetate.

Sunscreen actives may also be included in compositions of the present invention. These will be organic compounds having at least one chromophoric group absorbing within the ultraviolet ranging from 290 to 400 nm. Chromophoric organic sunscreen agents may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, alpha-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzone, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; Etocrylene; and 4-isopropyl-dibenzoylmethane). Particularly useful are: 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis (hydroxypropyl)]aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid and mixtures thereof.

Particularly preferred are such materials as ethylhexyl p-methoxycinnamate, available as Parsol MCX®, Avobenzene, available as Parsol 1789®, and Dermablock OS® (octylsalicylate).

Amounts of the organic sunscreen agent will range from about 0.1 to about 15%, preferably from about 0.5% to about 10%, optimally from about 1% to about 8% by weight of the composition.

Advantageously present may also be water-insoluble organic material in the form of polymeric porous spherical particles. By the term "porous" is meant an open or closed cell structure. Preferably the particles are not hollow beads. Average particle size may range from about 0.1 to about 100, preferably from about 1 to about 50, more preferably greater than 5 and especially from 5 to about 15, optimally from about 6 to about 10 μm. Organic polymers or copolymers are the preferred materials and can be formed from monomers including the acid, salt or ester forms of acrylic acid and methacrylic acid, methylacrylate, ethylacrylate, ethylene, propylene, vinylidene chloride, acrylonitrile, maleic acid, vinyl pyrrolidone, styrene, butadiene and mixtures thereof. The polymers are especially useful in cross-linked form. Cells of the porous articles may be filled by a gas which can be air, nitrogen or a hydrocarbon. Oil Absorbance (castor oil) is a measure of porosity and in the preferred but not limiting embodiment may range from about 90 to about 500, preferably from about 100 to about 200, optimally from about 120 to about 180 ml/100 grams. Density of the particles in the preferred but not limiting embodiment may range from about 0.08 to 0.55, preferably from about 0.15 to 0.48 g/cm$^3$.

Illustrative porous polymers include polymethylmethacrylate and cross-linked polystyrene. Most preferred is polymethyl methacrylate available as Ganzpearl® GMP 820 available from Presperse, Inc., Piscataway, N.J., known also by its INCI name of Methyl Methacrylate Crosspolymer.

Amounts of the water-insoluble polymeric porous particles may range from about 0.01 to about 10%, preferably from about 0.1 to about 5%, optimally from about 0.3 to about 2% by weight of the composition.

Preservatives can desirably be incorporated into the compositions of this invention to protect against the growth of potentially harmful microorganisms. Particularly preferred preservatives are phenoxyethanol, methyl paraben, propyl paraben, imidazolidinyl urea, dimethyloldimethylhydantoin, ethylenediaminetetraacetic acid salts (EDTA), sodium dehydroacetate, methylchloroisothiazolinone, methylisothiazolinone, iodopropynbutylcarbamate and benzyl alcohol. The preservatives should be selected having regard for the use of the composition and possible incompatibilities between the preservatives and other ingredients. Preservatives are preferably employed in amounts ranging from 0.01% to 2% by weight of the composition.

A variety of herbal extracts may optionally be included in compositions of this invention. The extracts may either be water soluble or water-insoluble carried in a solvent which respectively is hydrophilic or hydrophobic. Water and ethanol are the preferred extract solvents. Illustrative extracts include those from green tea, chamomile, licorice, aloe vera, grape seed, citrus unshui, willow bark, sage, thyme and rosemary.

Also included may be such materials as lipoic acid, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B and Ceramide 6) as well as pseudoceramides may also be useful. Amounts of these materials may range from about 0.000001 to about 10%, preferably from about 0.0001 to about 1% by weight of the composition.

Colorants, opacifiers and abrasives may also be included in compositions of the present invention. Each of these substances may range from about 0.05 to about 5%, preferably between 0.1 and 3% by weight of the composition.

Still other suitable actives for skin compositions and use in the present invention include creatine, resveratrol, hyaluronic acid (particularly those of molecular weight of around 800), and combinations thereof. Amounts may range from about 0.000001 to about 5%, preferably from about 0.001 to about 1% by weight of the compositions.

The following examples will more fully illustrate the embodiments of this invention. All parts, percentages and proportions referred to herein and in the appended claims are by weight unless otherwise illustrated.

EXAMPLES 1-8

Formulas suitable for the present invention are recorded in Table I.

TABLE I

| Component | Example (Weight %) | | | | | | | |
|---|---|---|---|---|---|---|---|---|
| | 1 | 2 | 3 | 4 | 5 | 6 | 7 | 8 |
| Cyclopentasiloxane | 20.00 | 20.00 | 0.00 | 0.00 | 0.00 | 10.00 | 10.00 | 10.00 |
| Cationic Copolymer (7688 MP) | 10.00 | 10.00 | 2.00 | 4.00 | 2.00 | 1.00 | 1.00 | 0.50 |
| Ethylhexyl Methoxycinnamate | 4.00 | 4.00 | 4.00 | 4.00 | 4.00 | 4.00 | 4.00 | 4.00 |
| Ethylhexyl Salicylate | 2.00 | 2.00 | 2.00 | 2.00 | 2.00 | 2.00 | 2.00 | 2.00 |
| Polysorbate 40 | 1.62 | 1.62 | 1.62 | 1.62 | 1.62 | 1.62 | 1.62 | 1.62 |
| Cetyl Alcohol | 1.55 | 1.55 | 1.55 | 1.55 | 1.55 | 1.55 | 1.55 | 1.55 |
| Dimethicone | 1.00 | 1.00 | 1.00 | 1.00 | 1.00 | 1.00 | 1.00 | 1.00 |
| Titanium Dioxide Coated | 1.00 | 0.80 | 0.80 | 0.80 | 1.20 | 1.20 | 1.00 | 0.80 |
| Polymethylmethacrylate Beads (Ganzpearl ® GMP 0820) | 0.80 | 0.80 | 0.80 | 0.80 | 0.80 | 0.40 | 0.60 | 1.00 |
| Glycerin Monostearate | 0.78 | 0.78 | 0.78 | 0.78 | 0.78 | 0.78 | 0.78 | 0.78 |
| Mica (Timiron ® MP111) | 0.50 | 1.00 | 1.00 | 1.00 | 0.80 | 0.80 | 0.40 | 0.20 |
| Silicone Elastomer | 3.50 | 3.50 | 0.50 | 0.50 | 0.50 | 1.50 | 1.50 | 1.50 |
| Mica (Satin Mica) | 0.50 | 0.50 | 0.50 | 0.50 | 1.00 | 0.50 | 0.50 | 1.00 |
| Stearic Acid | 0.25 | 0.25 | 0.25 | 0.25 | 0.25 | 0.25 | 0.25 | 0.25 |
| Cholesterol | 0.20 | 0.20 | 0.20 | 0.20 | 0.20 | 0.20 | 0.20 | 0.20 |
| Linoleic Acid | 0.10 | 0.10 | 0.10 | 0.10 | 0.10 | 0.10 | 0.10 | 0.10 |
| Water | Balance | Balance | Balance | Balance | Balance | Balance | Balance | Balance |

Compositions of the present invention may also contain vitamins. Illustrative water-soluble vitamins are Niacinamide, Vitamin $B_2$, Vitamin $B_6$, Vitamin C and Biotin. Among the useful water-insoluble vitamins are Vitamin A (retinol), Vitamin A Palmitate, ascorbyl tetraisopalmitate, Vitamin E (tocopherol), Vitamin E Acetate and DL-panthenol. Total amount of vitamins when present in compositions according to the present invention may range from 0.001 to 10%, preferably from 0.01% to 1%, optimally from 0.1 to 0.5% by weight of the composition.

Desquamation agents are further optional components. Illustrative are the alpha-hydroxycarboxylic acids and beta-hydroxycarboxylic acids and salts of these acids. Among the former are salts of glycolic acid, lactic acid and malic acid. Salicylic acid is representative of the beta-hydroxycarboxylic acids. Amounts of these materials when present may range from about 0.1 to about 15% by weight of the composition.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

All documents referred to herein, including all patents, patent applications, and printed publications, are hereby incorporated by reference in their entirety in this disclosure.

EXAMPLE 2

Radiance in the form of a gloss measurement was evaluated on a Novogloss® Glossmeter. The Glossmeter geometry was first set with both detector and light source at 85° from normal. An appropriate reflection standard was used to calibrate the instrument. Gloss (radiance) is reported as the percent difference in before and after treatment measurements. The larger the value (or less negative), the better the radiance effect.

A haze determination was utilized to evaluate soft focus effects. For this purpose, a Hunter Lab Spectracolorimeter was employed. This instrument had an optical geometry of 0° incidence and 45° reflectance (both for normal). Reflectance measurements gauge the soft focus effect from an opaque surface. These measurements are reported as a Haze value. It is the difference between an initial (zero) reading and a final one after treatment. Higher Haze values indicate a greater soft focus effect.

Sample formula in 20 mg dosage was applied onto a human forearm, and let dry for 20 minutes. Treated forearms were then rinsed under water for 2 minutes, and let dry for another 20 minutes. Thereafter the treated areas were scanned on the Hunter Lab Spectracolorimeter and also on the Glossmeter. Before and after changes were recorded both for pre-rinse and post-rinse conditions to obtain the respective percent Gloss and Haze values.

TABLE II

| Component | \multicolumn{14}{c}{Formula (Weight %)} | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Phase A | | | | | | | | | | | | | | |
| Disodium EDTA | 0.10 | 0.10 | 0.10 | 0.10 | 0.10 | 0.10 | 0.10 | 0.10 | 0.10 | 0.10 | 0.10 | 0.10 | 0.10 | 0.10 |
| Glycerin | 5.00 | 5.00 | 5.00 | 5.00 | 5.00 | 5.00 | 5.00 | 5.00 | 5.00 | 5.00 | 5.00 | 5.00 | 5.00 | 5.00 |
| Phase B | | | | | | | | | | | | | | |
| Promulgen D ® (Cetearyl Alcohol & Ceteareth 20) | 2.77 | 2.77 | 2.77 | 2.77 | 2.77 | 2.77 | 2.77 | 2.77 | 2.77 | 2.77 | 2.77 | 2.77 | 2.77 | 2.77 |
| PEG-100 Stearate | 1.85 | 1.85 | 1.85 | 1.85 | 1.85 | 1.85 | 1.85 | 1.85 | 1.85 | 1.85 | 1.85 | 1.85 | 1.85 | 1.85 |
| Ethylhexyl Methoxycinnamate | 6.00 | 6.00 | 6.00 | 6.00 | 6.00 | 6.00 | 6.00 | 6.00 | 6.00 | 6.00 | 6.00 | 6.00 | 6.00 | 6.00 |
| Caprylic/Capric Triglycerides | 2.75 | 2.75 | 2.75 | 2.75 | 2.75 | 2.75 | 2.75 | 2.75 | 2.75 | 2.75 | 2.75 | 2.75 | 2.75 | 2.75 |
| Stearic Acid | 0.46 | 0.46 | 0.46 | 0.46 | 0.46 | 0.46 | 0.46 | 0.46 | 0.46 | 0.46 | 0.46 | 0.46 | 0.46 | 0.46 |
| Cholesterol | 0.92 | 0.92 | 0.92 | 0.92 | 0.92 | 0.92 | 0.92 | 0.92 | 0.92 | 0.92 | 0.92 | 0.92 | 0.92 | 0.92 |
| Phase C | | | | | | | | | | | | | | |
| Titanium Dioxide | 2.00 | 2.00 | 2.00 | 2.00 | 2.00 | 2.00 | 2.00 | 2.00 | 2.00 | 2.00 | 2.00 | 2.00 | 2.00 | 2.00 |
| Phase D | | | | | | | | | | | | | | |
| Isohexadecane | 0.50 | 0.50 | 0.50 | 0.50 | 0.50 | 0.50 | 0.50 | 0.50 | 0.50 | 0.50 | 0.50 | 0.50 | 0.50 | 0.50 |
| Dimethicone | 0.25 | 0.25 | 0.25 | 0.25 | 0.25 | 0.25 | 0.25 | 0.25 | 0.25 | 0.25 | 0.25 | 0.25 | 0.25 | 0.25 |
| Phase G | | | | | | | | | | | | | | |
| Simulgel INS ® | — | 1.00 | 1.00 | 1.00 | — | — | — | — | — | — | — | 1.00 | — | — |
| Cationic Polymer 7688 MP | — | — | — | — | 1.00 | 1.00 | 1.00 | — | — | — | — | — | 1.00 | — |
| Merquat 5 ® | — | — | — | — | — | — | — | 1.00 | 1.00 | 1.00 | — | — | — | 1.00 |
| Phase H | | | | | | | | | | | | | | |
| Cyclopentasiloxane | 8.50 | 8.50 | 8.50 | 8.50 | 8.50 | 8.50 | 8.50 | 8.50 | 8.50 | 8.50 | 8.50 | 8.50 | 8.50 | 8.50 |
| Phase I | | | | | | | | | | | | | | |
| DC 9045 Silicone Elastomer | — | 5.00 | — | 5.00 | — | — | 5.00 | — | — | 5.00 | 5.00 | 5.00 | 5.00 | 5.00 |
| Timiron MP111 ® | — | — | 1.00 | — | — | 1.00 | — | — | 1.00 | — | 1.00 | 1.00 | 1.00 | 1.00 |
| Ganzpearl GMP 820 ® (Polymethylmethacrylate) | — | — | — | — | 1.00 | — | — | 1.00 | — | — | 1.00 | 1.00 | 1.00 | 1.00 |
| Phase J | | | | | | | | | | | | | | |
| DMDM Hydantoin/Iodopropynyl Butylcarbamate | 0.20 | 0.20 | 0.20 | 0.20 | 0.20 | 0.20 | 0.20 | 0.20 | 0.20 | 0.20 | 0.20 | 0.20 | 0.20 | 0.20 |
| Deionized Water | balance | balance | balance | balance | balance | balance | balance | balance | balance | balance | balance | balance | balance | balance |

TABLE III

| Optical Measurement Values After Application | | | | | | | | | | | | | | |
|---|---|---|---|---|---|---|---|---|---|---|---|---|---|---|
| % Gloss Change* | 8.7 | −38.2 | 43.5 | −10.3 | −30.1 | 49.8 | −8.3 | −45.7 | 37.8 | −12.3 | 5.1 | 11 | 17.2 | 8 |
| Haze | 6.3 | 36.4 | 8.1 | 12.7 | 37.8 | 9.2 | 13.7 | 36.3 | 8.2 | 12.6 | 71.3 | 71.2 | 73.7 | 70.1 |
| Optical Measurement Values After Rinsing the Application | | | | | | | | | | | | | | |
| % Gloss Change* | −0.2 | −1.4 | 1.1 | −0.6 | −30.1 | 47.6 | −7.7 | −19.1 | 29.8 | −3.1 | −1.6 | −0.8 | 16.1 | 4.7 |
| Haze | 1.2 | 2 | 1.3 | 1.1 | 36.3 | 7.2 | 11.5 | 22.2 | 2.8 | 7.3 | 1.1 | 2.2 | 70.2 | 37.8 |

*Initial Gloss value of untreated forearm was 11.4

Formula 1 is a control. A small effect on radiance/Gloss and soft focus/Haze was seen due to the presence of titanium dioxide. Formulas 2, 5 and 8 besides the base formula components (control) additionally included silicone elastomer and one each of the cationic copolymers. Identity of the copolymers are as follows. Merquat 5® is a trademark for Acrylamide/Methacryloyloxyethyl Trimethyl Ammonium Methylsulfate Copolymer; Simulgel INS® is a trademark for Hydroxyethylacrylate/Sodium Acryloyldimethyltaurate Copolymer; and Copolymer 7688 MP is a trademark for Acrylamide/Acryloylethyl Trimethylammonium Chloride/Tris(hydroxymethyl)acrylamidomethane Copolymer. All these formulas evidenced improvement in soft focus/Haze over the control. This benefit was particularly evident with formula 5 (that utilizes 7688 MP) for both the pre-rinse and post-rinse Haze values. Nonetheless, radiance for all three formulas as measured by the Gloss change was poor relative to the control.

Formulas 3, 6 and 9 represent the base composition with cationic copolymer and light reflecting platelet-shaped (LRPS) particles, but absent any silicone elastomer. Formula 6 (with 7688 MP) exhibited a significant radiance/Gloss benefit compared to the alternate copolymer formulas. Haze value also improved.

Formulas 4, 7 and 10 represent the base components with addition of cationic copolymer. Benefits in soft focus/Haze were evident but radiance/Gloss was inferior even to the control.

Formula 11 represents all components except the presence of cationic copolymer. Post-rinse gloss and haze value were no better than that of the control.

Formulas 12, 13 and 14 are fully formulated. These contain besides base components, a cationic polymer, silicone elastomer and LRPS particles. Formula 13 with 7688 MP as the copolymer exhibited exceptional soft focus/haze both in pre- and post-rinse evaluations. Formulas 12 and 14 also provided improvement in both benefits, but of a lesser magnitude than Formula 13.

What is claimed is:

1. A cosmetic composition comprising:
   (i) from about 0.01 to about 30% by weight of a crosslinked silicone elastomer;
   (ii) from about 0.1 to about 20% by weight of a cationic copolymer which is acrylamide/acryloylethyl trimethylammonium chloride/tris(hydroxymethyl)-acrylamidomethane copolymer;
   (iii) from about 0.1 to about 5% by weight of light reflecting platelet shaped particles; and
   (iv) a cosmetically acceptable carrier.

2. The composition according to claim 1 wherein the light reflecting inorganic platelet shaped particles have an average particle size of about 10,000 to about 30,000 nm.

3. The composition according to claim 1 wherein the light reflecting inorganic platelet shaped particles are selected from titanium dioxide coated mica or bismuth oxychloride.

4. The composition according to claim 1 further comprising from about 0.01 to about 10% by weight of porous particles of polymethylmethacrylate.

5. The composition according to claim 1 further comprising from about 0.05 to about 2% of a non-coated mica of volume average particle size ranging from 1,000 to 10,000 nm.

* * * * *